US008699726B2

(12) United States Patent
Steele et al.

(10) Patent No.: US 8,699,726 B2
(45) Date of Patent: Apr. 15, 2014

(54) APPARATUS AND METHOD FOR BIASING A TRANSDUCER

(75) Inventors: Colin Findlay Steele, Edinburgh (GB); Douglas James Wallace MacFarlane, Edinburgh (GB)

(73) Assignee: Wolfson Microelectronics plc, Edinburgh (GB)

( * ) Notice: Subject to any disclaimer, the term of this patent is extended or adjusted under 35 U.S.C. 154(b) by 961 days.

(21) Appl. No.: 12/649,525

(22) Filed: Dec. 30, 2009

(65) Prior Publication Data

US 2010/0166228 A1 Jul. 1, 2010

(30) Foreign Application Priority Data

Dec. 30, 2008 (GB) .................................. 0823674.7

(51) Int. Cl.
*H04R 3/00* (2006.01)
(52) U.S. Cl.
USPC ............................ 381/113; 381/111; 381/174

(58) Field of Classification Search
USPC .................................... 381/111–113, 92, 174
See application file for complete search history.

(56) References Cited

U.S. PATENT DOCUMENTS

| 4,486,821 | A | 12/1984 | Itakura |
| 2002/0153869 | A1 | 10/2002 | Kurotsu |
| 2005/0231127 | A1 | 10/2005 | Yamamoto et al. |
| 2006/0062406 | A1 | 3/2006 | Kinoshita |
| 2008/0075306 | A1 | 3/2008 | Poulsen et al. |
| 2009/0003629 | A1* | 1/2009 | Shajaan et al. ................ 381/113 |

* cited by examiner

*Primary Examiner* — Disler Paul
(74) *Attorney, Agent, or Firm* — Dickstein Shapiro LLP

(57) ABSTRACT

An apparatus comprising a capacitive transducer, for example a MEMS microphone. A first voltage generator is connected to receive a first voltage (VDD*) and generate a second voltage ($V_{CP}$) for biasing the capacitive transducer. A control circuit is adapted to, in use, control the first voltage (VDD*) based on a calibration value, wherein a different calibration value would lead to a different first voltage level and the calibration value is set such that an input signal of known amplitude produces an output signal of predetermined amplitude.

35 Claims, 5 Drawing Sheets

APPARATUS AND METHOD FOR BIASING A TRANSDUCER

BACKGROUND OF THE INVENTION

1. Field of the Invention

This invention relates to an apparatus and method for biasing a high input impedance device or circuitry, such as a capacitive transducer for example. In particular, the invention relates to the operation and adjustment or calibration of the output voltage of a voltage supply apparatus during, for example, the use or testing of such high input impedance devices or circuits.

2. Description of the Related Art

Consumer electronics devices are continually getting smaller and, with advances in technology, are gaining ever increasing performance and functionality. This is clearly evident in the technology used in consumer electronic products such as, for example, mobile phones, laptop computers, MP3 players and personal digital assistants (PDAs). Requirements of the mobile phone industry, for example, are driving components to become smaller with higher functionality and reduced cost. For example, some mobile phones now require multiple microphones for noise cancelling, or accelerometers to allow inertial navigation, while maintaining or reducing the small form factor and aiming at a similar total cost to previous generation phones.

This has encouraged the emergence of miniature transducers. For example, in respect to speech applications, initially electret microphones were used to capture speech, but more recently micro-electrical-mechanical (MEMS) transducers have been introduced. MEMS transducers may be used in a variety of applications including, but not limited to, pressure sensing, ultrasonic scanning, acceleration monitoring and signal generation. Such MEMS transducers may be capacitive transducers comprising one or more membranes with electrodes for read-out/drive deposited on the membranes and/or a substrate. Relative movement of these electrodes modulates the capacitance between them, which then has to be detected by associated electronic circuitry such as sensitive electronic amplifiers.

A complete MEMS device will typically comprise a MEMS transducer and associated electronic support circuitry including the amplifier.

As with the more conventional manufacturing technology that may be used for manufacturing the support circuitry, MEMS technology allows much of the manufacturing process to be performed on many devices at once, on a whole wafer containing thousands of devices, or even a batch of dozens of wafers. This fundamentally reduces production cost. Wafer-scale packaging techniques may also be used with similar benefits.

However, the production process contains many steps, not only the silicon-level processing steps for the transducer and the support circuitry, but also later steps, for example: placing the transducer on a common underlying substrate with the support circuitry; adding interconnects, such as bond wires for example, between the transducer and the electronics and from the electronics to terminals on the substrate; covering the assembly with protective material; and adding a case to cover the assembly. At each stage of manufacture, process variations may alter the characteristics, such as the acoustic sensitivity for example, of the capacitive (i.e. high impedance) transducer and/or the characteristics of the support circuitry, such as the power supply and amplifier circuitry. In particular, process variations can alter the overall sensitivity of a complete device such that a given acoustic stimulus will lead to different output signals being generated from nominally identical MEMS devices e.g. MEMS microphone devices.

Such variation in sensitivity is undesirable in the end application, particularly in applications where multiple high input impedance devices and circuits are used together (for example, the use of MEMS microphones in mobile phones or headphones that have noise cancelling circuitry that requires a plurality of said microphones). There is therefore a requirement for MEMS device manufacturers to produce devices with a small part-to-part spread of sensitivity, despite variability in the manufacturing processes. There is also a requirement for being able to calibrate, re-calibrate or normalise one or more MEMS devices, either individually or in relation to one another, either directly after production testing or sometime during use in the end application.

The sensitivity of a capacitive transducer may be proportional to the bias voltage imposed thereupon. So one method of adjusting the sensitivity is to adjust this bias voltage, generally in a final stage of manufacturing test, where a fixed physical stimulus is applied and the applied bias voltage adjusted until the required output amplitude is observed at the device output. The bias voltage is generally generated using a step-up voltage generator, such as a Dickson charge pump for example. However, the output voltage of open-loop voltage generators is generally variable with manufacturing tolerances, temperature and/or load current, so the bias voltage generated is not stable enough to generate a stable sensitivity. On the other hand, closed-loop voltage generators, where the voltage generator output is directly monitored and stabilised by a control loop, require control circuitry which increases the load on the output of the voltage generator itself, which adds components and hence cost, and also increases power consumption.

SUMMARY OF THE INVENTION

It is an aim of the present invention to provide an apparatus and a method for biasing or voltage supply of a high input impedance device or circuitry, such as a capacitive transducer for example.

Thus according to the present invention there is provided an apparatus for biasing a high impedance transducer comprising a first voltage generator configured to receive, in use, a first voltage and generate a second voltage for biasing the transducer, said second voltage having a stable relationship to said first voltage; and a control circuit configured to, in use, control the first voltage based on a calibration value, wherein a different calibration value would lead to a different first voltage level.

The present invention uses a first voltage generator which, when used to bias a high impedance device such as a capacitive transducer, generates a stable second voltage based on a first voltage. The output voltage of the first voltage generator, i.e. the second voltage, has a stable relationship to the input, i.e. the first, voltage. By stable relationship is meant that the ratio of the second voltage level to the first voltage level does not vary in normal operation. In other words the ratio of the first voltage level to the second voltage level is substantially constant across the range of normal operating conditions, i.e. expected ranges of voltages, temperatures, humidity etc. The first voltage generator is also stable in that it need not be controllable or programmable. The second voltage output of the first voltage generator is therefore predictable based on the first voltage supplied to the first voltage generator, i.e. the first voltage generator has a stable and predictable output and the second voltage has a stable and predictable relationship to the first voltage.

As the first voltage generator has a stable relationship between its input and output voltages the overall output voltage level of the apparatus can be controlled by controlling the voltage level input to the first voltage generator, i.e. the first voltage level.

The control circuit therefore controls the level of the first voltage, and hence the level of the second, output, voltage, using a calibration value. As will be described later this calibration value can be set so as to achieve a desired operating characteristic for a transducer. By appropriately adjusting the second voltage level, and hence the biasing voltage, the response of the transducer to a known stimulus can be controlled. A different calibration value leads to a different first voltage level and hence a different second voltage level. As will be described in more detail later the calibration value can be determined and set in a one-off calibration step, or the calibration value may be adjustable, allowing for periodic or, in some applications, continuous recalibration.

As mentioned above, due to the first voltage generator being arranged to have a stable and predictable relationship between the first and second voltages, the control circuit need only control the first voltage. The control circuit may therefore be connected to the input of the first voltage generator and not be connected to the output of the first voltage generator. Hence, there is no need to introduce a load onto the high voltage output of the first voltage generator. The control circuit is connected on the input side of the first voltage generator only. In others words the control circuit is electrically connected to the circuitry that feeds to the input of the first voltage generator and is not electrically connected to the output of the voltage generator. It will be appreciated that the term input side refers to functional connections and not physical layout.

An embodiment of the present invention therefore generally relates to an apparatus for biasing a high impedance device, such as a transducer, which has a first voltage generator which generates an output voltage based on an input voltage, the output voltage having a stable relationship to the input voltage wherein control circuitry operating purely on the input voltage, controls the input voltage so as to provide a particular output voltage.

The control circuit may comprise a second voltage generator for generating the first voltage and a feedback circuit. The second voltage generator is thus a different voltage generator to the first voltage generator. The second voltage generator may receive a third voltage, for instance a reference voltage, for use in generating the first voltage, the level of the first voltage being controlled, via the feedback circuit, by the first voltage level and the calibration value. This embodiment of the present invention thus has a feedback circuit but the feedback circuit operates on the output of second voltage generator to control the first voltage which is then input to the first voltage generator. The first voltage signal is conveniently a relatively low voltage. This embodiment of the present invention thus has a two stage voltage generation apparatus. The second voltage generator generates the first voltage which is input to the second voltage generator. The control circuit operates on the relatively low voltage second voltage generator to provide accurate control of the first voltage. This first voltage is then used in the first voltage generator which generates the relatively high voltage second voltage.

In one embodiment the feedback circuit comprises an adjustable potential divider circuit comprising a first resistive value and a second resistive value connected in series between the first voltage and a first reference voltage, such as ground. The value of at least one of the first resistive value and second resistive value is adjusted using the calibration value. A node connecting the first resistive value and the second resistive value provides a feedback signal for controlling the second voltage generator.

The second voltage generator may comprise an amplifier coupled to receive, in use, the third voltage as a supply voltage, the amplifier comprising: a first input terminal coupled to a second reference voltage; a second input terminal coupled to the feedback signal; and an output terminal providing the first voltage.

Alternatively the second voltage generator may comprise: a transistor connected in series between the third voltage and the first voltage; and an amplifier comprising: a first input terminal coupled to a second reference voltage; a second input terminal coupled to the feedback signal; and an output terminal for controlling the transistor.

The adjustable potential divider circuit may comprise an array of resistive values configurable to provide the first resistive value and the second resistive value of the adjustable potential divider circuit. The apparatus may further comprise a plurality of switches, the plurality of switches being controlled by the calibration value to provide the first and second resistive values of the adjustable potential divider circuit.

The apparatus may include a transducer biased by the second voltage and the calibration value may be set such that the transducer has a calibrated response, i.e. such that for a particular input stimulus to the transducer it produces a known response. The calibration value may be set such that the transducer produces the same output response as another transducer in response to the same stimulus, i.e. the calibration value could be set so as to standardise the response of different transducers.

The calibration value may be derived from test equipment coupled to the output of the transducer. As is known test equipment may be used to provide standard stimuli to transducers and to measure the response. The transducer apparatus could be tested whilst coupled to such test equipment and a calibration value derived. This calibration step could be performed once only in an initial set up process or the device may be periodically recalibrated.

The calibration value may be stored in a memory device, for instance a memory device of the type comprising a random access memory (RAM), programmable read only memory (PROM), erasable programmable read only memory (EPROM), electrically erasable programmable read only memory (EEPROM), flash memory or field programmable gate array (FPGA), or one or more fuse devices. The skilled person will appreciate that some memory devices are single use devices, i.e. one the calibration value is set it can not updated, and that such devices are therefore only suitable for an application where a single initial calibration is required. Other memory devices may be reconfigurable however and the calibration value could be updated periodically in recalibration. Where a single device comprises more than one transducer the memory device could hold a calibration value for each such transducer. In this way separate transducers can be calibrated separately and the calibration value for each transducer stored in a common memory device.

In another arrangement, the calibration value may be derived directly from an output signal of the transducer.

The transducer may be a capacitive transducer and, in one embodiment, may be a MEMS microphone.

In one embodiment the first voltage generator is a charge pump, such as a capacitive charge pump. The charge pump may, as is known, comprise a number of stages, with each stage arranged to pump the subsequent stage so as to increase the voltage. As explained in more detail below, when biasing loads such as capacitive transducers, which can be seen as high impedance loads, little current is drawn during normal usage. With such low current operation a charge pump can provide a voltage generator with a stable and predictable relationship between its input and output voltage.

The apparatus of the present invention may be used in a variety of applications. In particular, but not exclusively, the apparatus may be comprise one of an ultrasound imager, a sonar transmitter and/or receiver, a mobile phone or other communication device, a personal desktop assistant, an MP3 player or other personal audio device or a laptop computer.

In another aspect, the present invention provides an apparatus for driving a high impedance transducer comprising a charge pump having, in use, a stable relationship between input voltage and output voltage and a control circuit for controlling the level of the input voltage so as to control the level of the output voltage.

All of the advantages and embodiments described above in relation to the first aspect of the invention also apply to this aspect of the invention. In particular the control circuit is conveniently connected to the input of the charge pump and is not connected to the output of the charge pump and may be connected on the input side of the charge pump only.

In a further aspect of the invention there is provided a method of biasing a transducer which, in use, receives an input signal and produces an output signal, the method comprising the steps of: providing a first voltage generator, the first voltage generator connected to receive a first voltage and generate a second voltage for biasing the transducer such that the second voltage has a stable relationship to the first voltage; and controlling the first voltage based on a calibration value, wherein a different calibration value would lead to a different first voltage level.

The method of the present invention thus arranges for a first voltage generator to have a stable and predictable relationship between its input and output voltages, i.e. the first and second voltages respectively. As described above this means that the first and second voltage have a set ratio which does not vary in operation of the device, i.e. the ratio of the first voltage to the second voltage is constant across normal operating ranges of voltage, temperature, humidity etc.

The controlling step conveniently comprises the steps of: providing a second voltage generator for generating the first voltage, the second voltage generator receiving a third voltage; and controlling the second voltage generator using the calibration value and the first voltage. The method thus involves arranging a controllable voltage generator to feed into a stable voltage generator in a two stage process. Control is performed at relatively low voltages with no unnecessary loading on the relatively high voltage output.

Conveniently the step of controlling further comprises the steps of: providing an adjustable potential divider circuit comprising a first resistive value and a second resistive value connected in series between the first voltage and a first reference voltage (GND); adjusting the value of at least one of the first resistive value and second resistive value using the calibration value; and using a node connecting the first resistive value and the second resistive value as a feedback signal ($V_{F*}$) for controlling the second voltage generator.

The step of providing a second voltage generator for generating the first voltage may comprise the steps of: providing an amplifier connected to receive the third voltage as a supply voltage; coupling a second voltage reference to a first input terminal of the amplifier; coupling the feedback signal to a second input terminal of the amplifier; and using the output of the amplifier as the first voltage. Alternatively the step of providing a second voltage generator may comprise the steps of: providing a transistor connected in series between the third voltage and the first voltage; and providing an amplifier comprising a first input terminal coupled to a second reference voltage and a second input terminal coupled to the feedback signal; and controlling the transistor using an output of the amplifier.

Adjusting the potential divider circuit conveniently comprises configuring an array of resistive values to provide the first resistive value and the second resistive value of the adjustable potential divider circuit. The method may also comprise providing a plurality of switches, and controlling the plurality of switches using the calibration value to provide the first and second resistive values of the adjustable potential divider circuit.

As described above the calibration value may be derived during a test procedure from test equipment connected to the output of the transducer. The calibration value may be stored, and hence received in use from a memory device of the type comprising a random access memory (RAM), programmable read only memory (PROM), erasable programmable read only memory (EPROM), electrically erasable programmable read only memory (EEPROM), flash memory or field programmable gate array (FPGA), or one or more fuse devices. The calibration value may also be received directly from an output signal of the transducer.

Again the transducer may a capacitive transducer, such as a MEMS microphone.

Conveniently the first voltage generator is a charge pump.

The present invention also relates to a method of calibrating an apparatus having a transducer. Thus according to a further aspect of the invention there is provided a method of calibrating an apparatus having a transducer which, in use, receives an input signal and produces an output signal, the method comprising the steps of: providing a first voltage generator, the first voltage generator connected to receive a first voltage and generate a second voltage for biasing the capacitive transducer; applying at least one test signal to the transducer and monitoring the response; and setting a calibration value in a control circuit, the control circuit controlling the first voltage based on the calibration value.

The method according to this aspect of the invention therefore derives a calibration from at least one test signal applied to the device and uses this calibration value to control the first voltage level—and hence the second voltage level and the bias voltage applied to the transducer. The test signal may be a defined test signal applied during a calibration stage, for instance when the apparatus is coupled to some test equipment. However the test signal in some applications could be a signal of opportunity that arises from operation of the apparatus.

As described above in relation to the other aspects of the invention the control circuit is conveniently connected on the input side of the first voltage generator only.

The control circuit may comprise a second voltage generator for generating the first voltage, the second voltage generator receiving, in use, a third voltage, and a feedback circuit for controlling the second voltage generator based on the calibration value and the first voltage. The feedback circuit may comprise: an adjustable potential divider circuit comprising a first resistive value and a second resistive value connected in series between the first voltage and a first reference voltage, a node connecting the first resistive value and the second resistive value providing a feedback signal for controlling the second voltage generator; wherein the step of setting the calibration value comprises adjusting at least one of the first resistive value and second resistive value.

The adjustable potential divider circuit may comprise an array of resistive values configurable to provide the first resistive value and the second resistive value of the adjustable potential divider circuit and the step of setting the calibration value comprises configuring said resistive values. The adjustable potential divider may further comprise a plurality of switches, and the step of setting the calibration value comprises activating at least some of said switches to provide the first and second resistive values of the adjustable potential divider circuit.

The step of setting the calibration value conveniently comprises storing the calibration value in a memory device of the type comprising a random access memory (RAM), programmable read only memory (PROM), erasable programmable read only memory (EPROM), electrically erasable programmable read only memory (EEPROM), flash memory or field programmable gate array (FPGA), or one or more fuse devices.

BRIEF DESCRIPTION OF THE DRAWINGS

For a better understanding of the invention, and to show more clearly how it may be carried into effect, reference will now be made, by way of example only, to the accompanying drawings in which:

FIG. 4b shows a charge pump stage in the charge pump of FIG. 4a;

DETAILED DESCRIPTION OF THE PREFERRED EMBODIMENTS

The description of the embodiments below will be made in relation to a high input impedance transducer in the form of a MEMS capacitive microphone. However, it will be appreciated that the invention is also applicable to other types of high input impedance transducers, devices, circuits, components and the like and not only MEMS capacitive transducers and not only microphones or audio applications. It is also noted that the detailed description will be made with reference to a voltage generator in the form of a charge pump, although it will be appreciated that the invention is equally applicable to other forms of voltage generating circuits. Furthermore, although the embodiments below will be described mainly in relation to fine tuning, trimming or adjusting (e.g. calibrating) a voltage generator during a testing or manufacturing stage, the invention is equally applicable to fine tuning, trimming or adjusting a voltage generator at any stage including, for example, during the use, i.e. post-testing, of the device in an end application.

Figure 1:
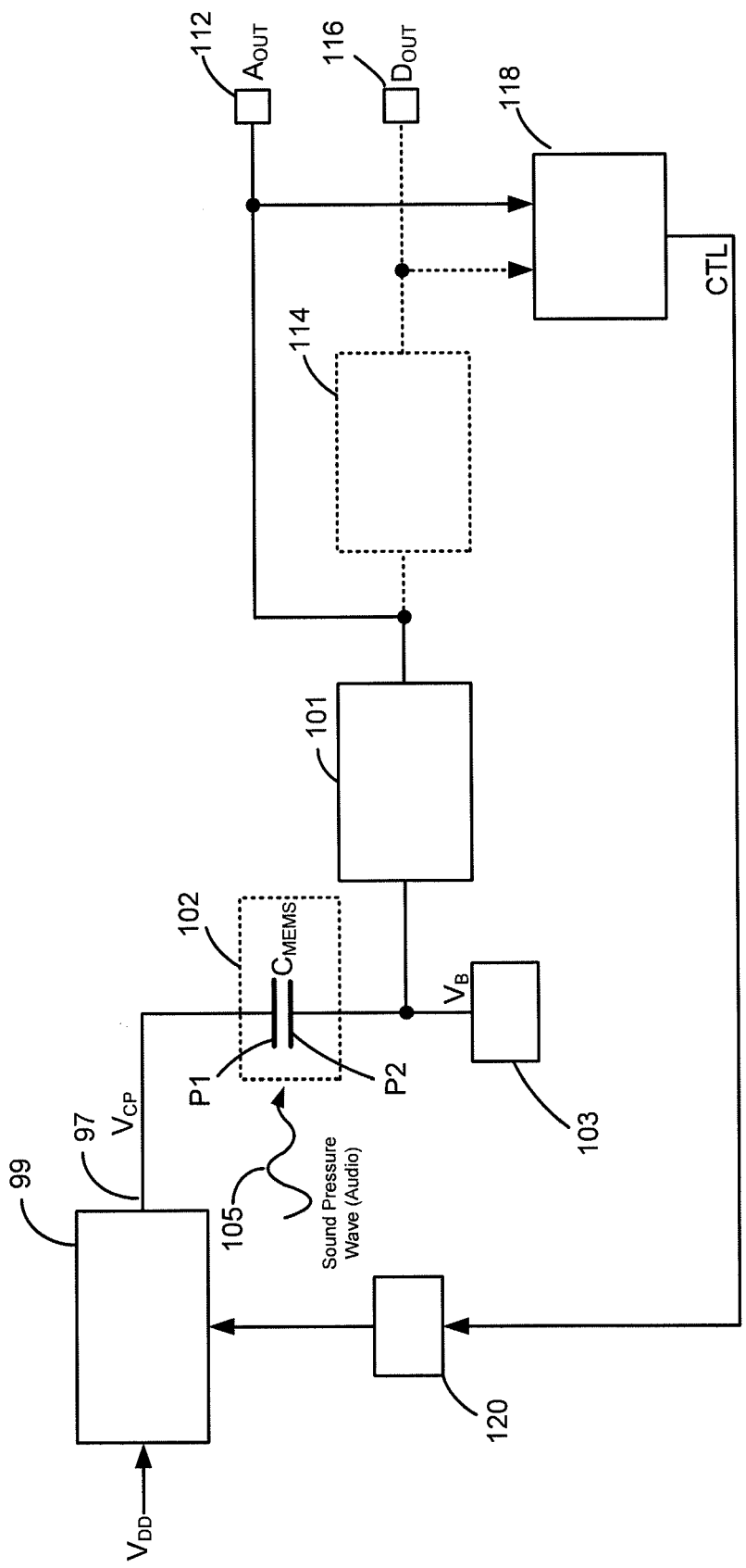
FIG. 1 is a schematic diagram of a MEMS transducer interfaced with electronic circuitry and connected to a voltage generator.

With reference to FIG. 1, the output terminal 97 of a voltage generator such as a charge pump 99, for example a Dickson type charge pump, is connected to a first capacitive plate P1 of a capacitive transducer such as a micro-electro-mechanical (MEMS) microphone 102 comprising said first capacitive plate P1 and a second capacitive plate P2, which form a capacitor $C_{MEMS}$. Either one of the capacitive plates may be formed by a first electrode mechanically coupled to a generally rigid structural layer or back-plate. The other capacitive plate may be formed by a second electrode mechanically coupled to a flexible membrane. The flexible membrane is free to move in response to pressure differences generated by sound waves that are incident on the MEMS microphone.

The second plate P2, i.e. the low-voltage side, of the capacitor $C_{MEMS}$ is connected to electronic circuitry that buffers and processes a signal received from the MEMS microphone 102. In the example shown, the second plate P2 of the capacitor $C_{MEMS}$ is connected to the input of an amplifier 101 and a bias circuit 103. Both the input of the amplifier 101 and the second plate P2 of the capacitor $C_{MEMS}$ are biased to a bias voltage $V_B$ by means of the bias circuit 103. The bias circuit 103 and the input of the amplifier 101 preferably present a high input impedance to the capacitor $C_{MEMS}$ to avoid attenuating the MEMS microphone signal (which has an audio frequency, for example). Suitable amplifier and bias circuitry, which is application dependant, is known in the art.

The output of the amplifier 101 can be connected to a first output terminal 112 for outputting an amplified analogue signal $A_{OUT}$ representing the signal voltage from the MEMS microphone 102. The output of the amplifier 101 may also be connected to an analogue-to-digital converter (ADC) 114. The ADC 114 converts the analogue output signal of the amplifier 101 into a corresponding digital signal $D_{OUT}$ for output on a second output terminal 116. It will be appreciated that the ADC 114 is not necessarily on the same integrated circuit as the LNA 106. In addition, it will be appreciated that the provision of both analogue and digital output signals $A_{OUT}$, $D_{OUT}$ or 112, 116 terminals is not always necessary.

The charge pump 99 supplies a voltage $V_{CP}$ to bias the first plate P1, i.e. the high-voltage side, of the capacitor $C_{MEMS}$. In response to incident sound waves on the MEMS microphone 102, the plate that constitutes the flexible membrane of the capacitor $C_{MEMS}$ is deformed slightly from its equilibrium position. The distance between the first and second capacitive plates (P1, P2) of the capacitor $C_{MEMS}$ is correspondingly altered, giving rise to a change ($\Delta C$) in capacitance between the two plates (P1, P2). For example, when the plate that constitutes the flexible membrane is deformed towards the plate that constitutes the fixed plate, the capacitance of the capacitor $C_{MEMS}$ is increased.

Assuming the impedance of the input of the amplifier 101 and the bias circuitry 103 are high compared to the impedance of the capacitor $C_{MEMS}$ at the signal frequency (for example audio frequency), the charge on the capacitor $C_{MEMS}$ remains constant. Thus, when the capacitance between the two plates P1, P2 is changed by an amount $\Delta C$, the voltage across the capacitor $C_{MEMS}$ has to reduce by an amount $\Delta V$, where $$\Delta V = (V_{CP} - V_B) \cdot (\Delta C / C_{MEMS})$$

Assuming the voltage $V_{CP}$ output by the voltage generator 99 remains constant, the voltage seen at the bottom plate P2 of the capacitor $C_{MEMS}$ is correspondingly changed by the amount $\Delta V$. This change in voltage $\Delta V$, which is representative of the incident sound wave, is subsequently received and processed by the amplifier 101.

As discussed above, each MEMS device, i.e. transducer and other associated circuitry, suffers from manufacturing variations such that for a given bias voltage (for example $V_{CP}$, $V_B$) and a given stimulus applied to different MEMS microphones 102, different output signals are observed at the outputs 112 or 116 of the device. There will also be manufacturing variations that will cause variation in the bias voltages $V_{CP}$, $V_B$ and in the gain of the amplifier 101 and also of the ADC 114 if present, which will also cause variations in sensitivity as observed at the outputs 112 or 116 of the device.

The acousto-electric sensitivity of a MEMS microphone 102 is proportional to the voltage bias $V_x$ applied across its plates P1, P2: where $V_x = V_{CP} - V_B$. Therefore, by adjusting the output voltage $V_{CP}$ of the voltage generator 99, compensation may be made for: (a) manufacturing and/or operational variations of the transducer 102; (b) manufacturing and/or operational variations of the voltage generator 99 itself; (c) manufacturing and/or operational variations of the bias circuit 103; (d) variations in the gain of the amplifier 101; and/or (e) variations in the full-scale range of the ADC 114 if present.

In one form of testing using automated test equipment, the first and/or second output terminals 112, 116 are connected as shown in FIG. 1 to automatic test equipment 118 (ATE) which monitors the first and/or second output signals $A_{OUT}$, $D_{OUT}$.

During such testing, acoustic stimulus 105 of known amplitude is applied to the transducer 102, and the amplitude of the output signal ($A_{OUT}$, $D_{OUT}$) measured, and compared to a reference amplitude corresponding to the desired sensitivity. The ATE 118 then adjusts a calibration value CTL, which may be a digital control signal, which is input, either directly or indirectly, to a variable voltage generator 99 so as to increase or decrease its output voltage $V_{CP}$. The response to the acoustic stimulus may then be measured again, and the ATE 118 will adjust the calibration value CTL again, until the output signal ($A_{OUT}$, $D_{OUT}$) is within a specified tolerance of the required, i.e. reference, amplitude. The calibration value CTL may be stored within a device 120 at the end of the test procedure by programming fuses or stored in some other memory circuit, so that the output voltage $V_{CP}$ of the charge pump 99, and hence the MEMS device sensitivity, is retained when the MEMS device is removed from the ATE 118 and later used in the end application.

This adjustment method, by means of the calibration value CTL, requires a programmable charge pump 99, for example a digitally controlled charge pump 99. As will be familiar to a person skilled in the art, a charge pump 99, for example a Dickson charge pump, may comprise a number of stages for boosting a low input voltage into a much higher output voltage, for example, increasing a 1.2 v (VDD) input voltage to a 12 v output voltage ($V_{CP}$) using 10 stages (each stage boosting the voltage by 1.2 v). A controller (not illustrated) may be connected to the charge pump 99 and used to alter the number of stages used in the charge pump 99. The output voltage $V_{CP}$ of the charge pump 99 is increased by increasing the number of stages of the charge pump 99 and, similarly, the output voltage $V_{CP}$ of the charge pump 99 is decreased by decreasing the number of stages of the charge pump 99. However, this form of adjustment has the disadvantage in that it only allows the output voltage $V_{CP}$ to be adjusted coarsely: in steps of 1.2 v for the above example, which may not allow enough resolution in the adjusted sensitivity.

Although not illustrated, one alternative scheme for a charge pump driving a capacitive transducer is to drive the input stage of the charge pump with a resistive pass device, such that the width of the clock pulse applied to the charge pump is altered, in accordance with the test, so that the input stage is only partly charged. Therefore, the input stage is not charged up to the full 1.2V, but alternatively to some lower voltage depending on the programmed i.e. stored, pulse width. However, such a scheme is sensitive to the resistance of the pass device, which will vary with temperature and the applied switching supply voltage, so will not provide a stable enough charge pump output voltage, which means that the adjusted sensitivity may drift with temperature or time.

To avoid the issues of limited resolution or output sensitivity drift inherent in these open-loop implementations, a closed-loop charge pump may be used, where the actual output voltage of the charge pump is directly monitored by a feedback circuit which controls the charge pump, for example by altering the pulse width applied to the charge pump.

Figure 2:
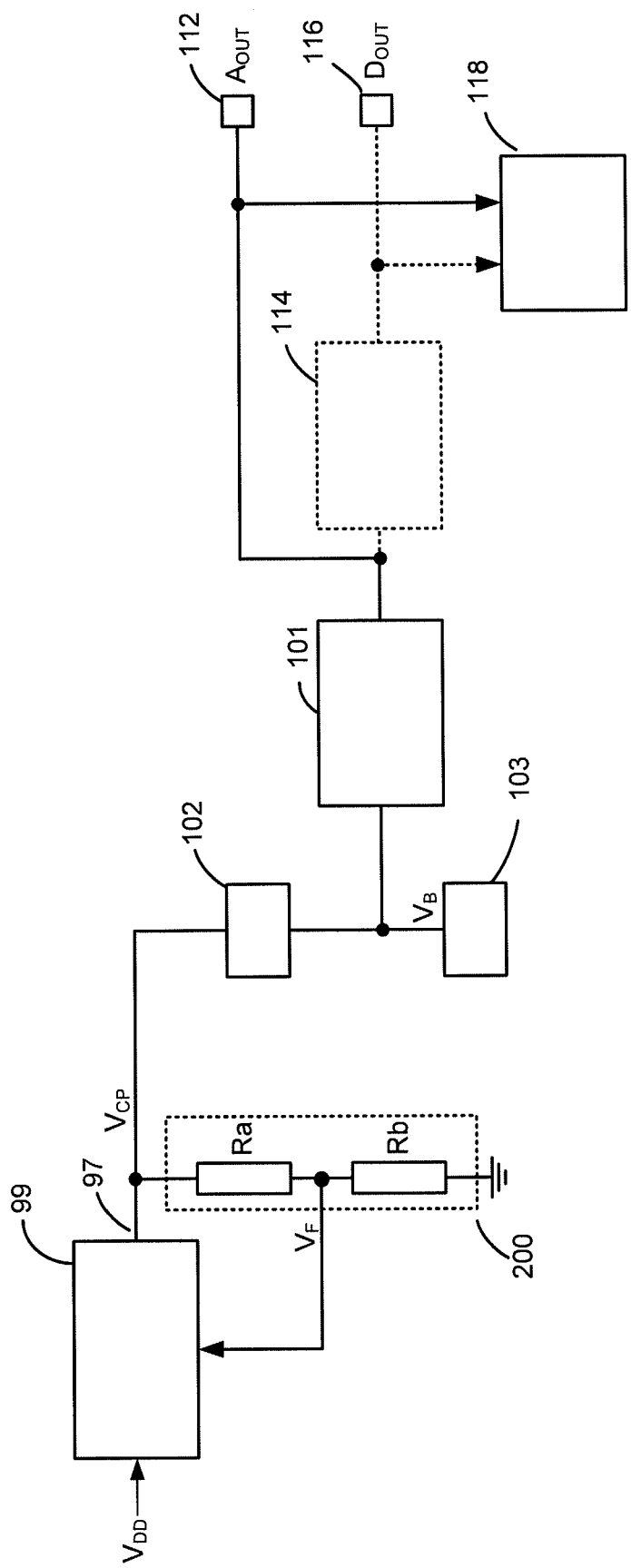
FIG. 2 is a schematic diagram of a MEMS transducer interfaced with electronic circuitry and connected to a voltage generator, where the output voltage of the voltage generator is adjusted according to a first method.

FIG. 2 shows such a closed-loop system, wherein a feedback circuit 200 comprises a potential divider that comprises first and second series connected resistors $R_a$ and $R_b$. The feedback circuit 200 outputs a feedback signal, in the form of a voltage $V_F$. This feedback signal $V_F$ is compared to a reference voltage $V_R$ (not illustrated), and the difference signal is used to modulate the charge pump output voltage $V_{CP}$, by altering the pulse width applied to a resistive input switch as described above. In this way, the output voltage $V_{CP}$ of the charge pump 99 settles to a value:

$$V_{CP} = V_R \cdot Rb/(Ra+Rb).$$

In order to alter the charge pump output voltage $V_{CP}$, the feedback circuit 200 may be implemented as a digitally controlled potential divider, for example as a string of resistive elements with the voltage $V_F$ being derived from a digitally chosen one of a bank of switches attached to various taps along this string. Thus, the charge pump output voltage $V_{CP}$, and hence the device sensitivity, can be adjusted depending on the MEMS device being tested to give the required sensitivity.

However, a disadvantage of this method is that the feedback circuit 200 (i.e. comprising the potential divider circuit) creates a significant load on the output node 97 of the charge pump 99. For example, if the output voltage $V_{CP}$ of the charge pump is +12V and the resistance value of the potential divider circuit is 200KΩ (a much higher value resistor would occupy a large chip area), the current that flows through the potential divider to ground equates to 60 µA (i.e. 12V/200KΩ), whereas the current that flows across the relatively higher input impedance MEMS microphone 102 is due only to that associated with parasitic leakage paths associated with the MEMS microphone 102, and as such is only in the order of picoAmps (pA) or sub-pA. Thus, not only does the inclusion of a feedback circuit 200 dramatically increase the load current, and hence increase the system power consumption, but it also requires the charge pump 99 to be designed to be capable of supplying 60 uA. Thus, the elements of the charge pump 99, for example the pump capacitors and possibly the diode elements have to be larger than otherwise necessary, which increases chip area and may increase the power consumption of the charge pump 99 even further.

In its broadest sense, the invention is concerned with controlling the output voltage of a voltage generator by controlling the input voltage to the voltage generator. The inventor has realised that in the application of driving a capacitive or high impedance node, the load on the voltage generator is light i.e. relatively very little current is required to be sourced by the voltage generator, and that by using a suitably designed voltage generator that has predictable and stable operational qualities in such an application, it is in fact possible to control the output voltage from the voltage generator by controlling its input voltage.

The invention avoids the disadvantages mentioned above in connection with the prior art. In particular, the invention has the advantage of not having to unnecessarily load the output of the voltage generator. The invention also has the advantage of enabling a lower power voltage generator to be provided.

Figure 3:
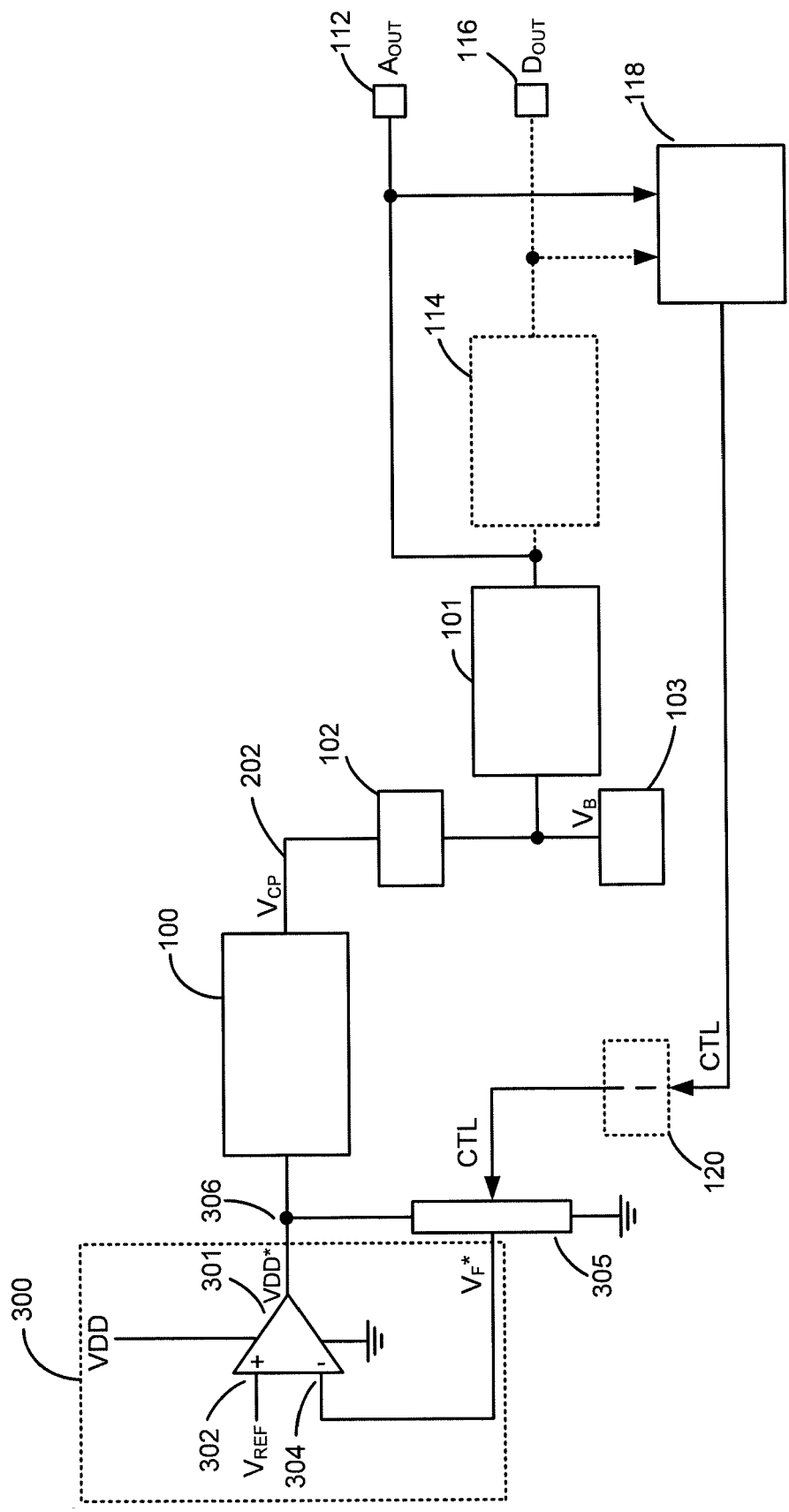
FIG. 3 is a schematic diagram of a MEMS transducer interfaced with electronic circuitry and connected to a voltage generator, where the output voltage of the voltage generator is adjusted according to an embodiment of the present invention.

Referring to FIG. 3, according to an embodiment of the invention the input voltage VDD* (also referred to hereinafter as a first voltage, for example 1.2V) to a first voltage generator 100 is supplied from a second voltage generator 300, for example comprising an amplifier 301. The first voltage generator 100, for example a charge pump, produces an output voltage (also referred to hereinafter as a second voltage, for example 12v) for biasing the transducer, e.g. a MEMS microphone. The amplifier 301 receives a supply voltage $V_{DD}$ (also referred to hereinafter as a third voltage, say 1.5V).

The amplifier 301 has a first input terminal, for example the non-inverting input 302, coupled to receive a reference voltage $V_{REF}$. This reference voltage $V_{REF}$ is a stable reference voltage, for example supplied from a bandgap voltage reference generator (not illustrated). The amplifier 301 has a second input terminal, for example the inverting input 304, coupled to receive a feedback voltage $V_{F*}$ from an adjustable potential divider circuit 305. The adjustable potential divider circuit 305 is connected between the output 306 of the amplifier 301 (i.e. the first voltage VDD* input to the voltage generator 100) and a reference voltage such as ground. The ratio of the potential divider circuit is varied according to a calibration value. According to one embodiment the calibration value is based on a control signal CTL received from the automatic test equipment 118. This enables the output of the amplifier 301 to be tuned (i.e. varied) according to the calibration value received from the automatic test equipment 118. In particular, the amplifier 301 and adjustable potential divider circuit 305 form a control circuit that is adapted, in use, to control the first voltage (VDD*) based on a calibration value, wherein a different calibration value would lead to a different first voltage level. The calibration value may be set such that the MEMS microphone has a desired response to a known stimulus.

In this way, the input voltage supplied to the first voltage generator 100 (i.e. voltage VDD*) can be controlled by setting the calibration value, thus compensating for any manufacturing variations in the MEMS microphone 102 and/or other manufacturing variations in the electronic circuitry. The calibration may be derived during testing to allow such manufacturing variations to be corrected for in a testing or calibration phase. Or in other words, the voltage VDD* supplied to the voltage generator 100 is controlled by a calibration value CTL that may be derived from, or based on, the output signal of the MEMS microphone 102.

The calibration value CTL for controlling the adjustment of the potential divider circuit 305 is not limited to being provided, either directly or indirectly from the test equipment 118. Indeed, in use from the calibration value may be provided on-chip and/or in system fuses or some other form of memory 120.

The potential divider circuit 305 may be implemented comprising a plurality of resistors connected in series (and/or parallel) with switches for enabling the respective first and second values of the potential divider circuit 305 to be selected. The skilled person will understand how to arrange such a resistive array so that the resistive values may be selected. As such, the potential divider circuit 305 is able to adjust the amount of output voltage VDD* that is fed back to the inverting input 304 of the amplifier 301 based on the calibration value CTL received from the tester 118 during testing or, when in use, the memory 120.

According to one embodiment, the calibration value CTL received from the ATE 118 during testing is used to configure an array of resistors forming the potential divider 305, for example by controlling a bank of corresponding switches, or blowing certain fuses provided in the circuit. The invention is also intended to embrace other arrangements for configuring the potential divider circuit 305. For example, a memory of the type comprising a Look-Up-Table (LUT), a random access memory (RAM), programmable read only memory (PROM), erasable programmable read only memory (EPROM), electrically erasable programmable read only memory (EEPROM), flash memory or field programmable gate array (FPGA) can be provided to control an array of switches associated with the potential divider circuit 305, thereby enabling a range of first and second resistive values to be selected in the potential divider circuit 305.

Some of the above forms of memory may be re-programmed, having the advantage of enabling the voltage generator 100 to be re-tuned, re-trimmed or re-calibrated, for example during use, allowing a method for calibration or normalisation of multiple microphones in the end-user system.

The invention has the advantage of enabling the bias voltage $V_{CP}$ generated by the voltage generator 100 to be adjusted, for example during a testing and/or re-calibration operation, without loading the output 202 of the voltage generator 100, and without requiring direct access to the output node 202 of the voltage generator 100. This means that the voltage generator 100 can be designed to have a smaller size than a corresponding generator designed to drive a feedback circuit as shown in FIG. 2. Furthermore, by avoiding any load on the output 202 of the voltage generator 100 the start-up time is also improved. The invention also has the advantages of neither requiring any high voltage components nor any complex control of the voltage generator 100, for example as described in FIG. 1.

Figure 4A:
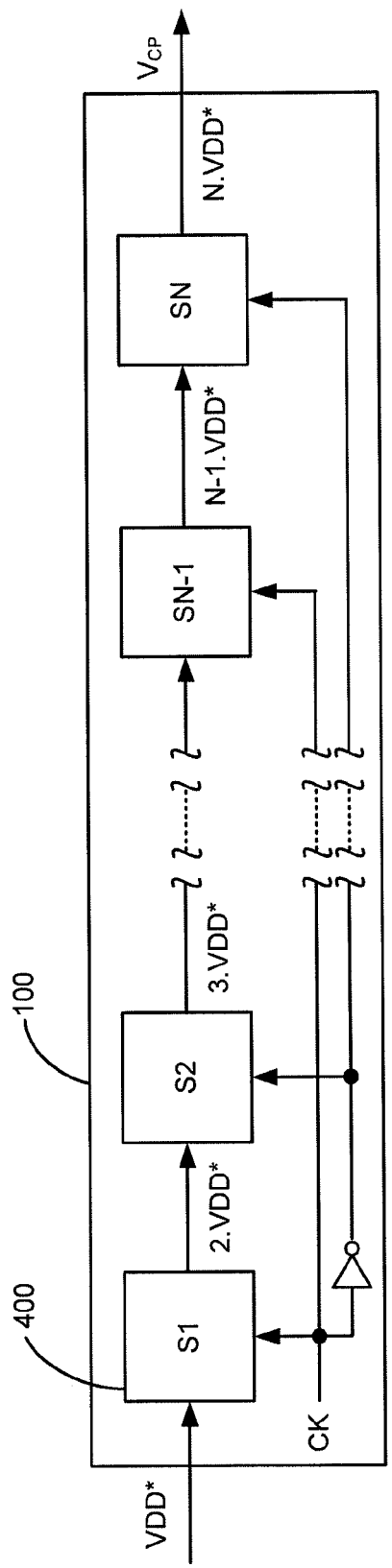
FIG. 4a is a schematic diagram of a charge pump that may be used as the voltage generator of FIG. 3.

FIG. 4a illustrates a basic block diagram of a voltage generator 100 in the form of a charge pump, suitable for use in an embodiment of the present invention. The charge pump 100 comprises a series S1-SN of similar charge pump stages 400. Ignoring switching losses, each stage S1-SN of the charge pump 100 successively increases its respective input voltage by an amount VDD*, dependent on the detailed design of each stage as will be readily understood by those skilled in the art. Thus, in the example shown in FIG. 4a, the first stage S1 receives an input voltage VDD* and pumps, i.e. increases, this voltage VDD* such that it provides an output voltage (VDD*+VDD*). The second stage S2 receives as its input voltage 2.VDD* and pumps this voltage such that it provides an output voltage of (2.VDD*+VDD*), and so on and so forth for each consecutive stage $S_N$ (where N is an integer greater than 1). Thus stage $S_N$ receives as an input voltage (N−1).VDD* and provides an output voltage of N.VDD*

Figure 4B:
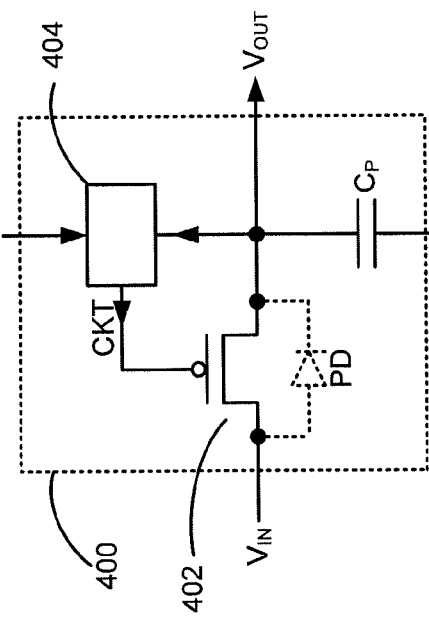

FIG. 4b illustrates a circuit diagram of a charge pump stage 400 of the charge pump 100 illustrated in FIG. 4a, suitable for use in an embodiment of the present invention. The charge pump stage 400 comprises: a transistor switch 402, for example a PMOS type transistor; a pumping capacitor $C_P$; and a level shift circuit 404.

The source terminal of the transistor 402 receives an input voltage $V_{IN}$ and outputs a "pumped" output voltage $V_{OUT}$ via its drain terminal. The gate terminal of the switch transistor 402 is controlled by a transistor control signal CKT that is output from the level shift circuit 404. The level shift circuit 404 is connected to the source terminal of the transistor 402 such that it receives the output voltage $V_{OUT}$. The level shift circuit 404 also receives a slave control signal CK*. The source terminal of the transistor 402 is also connected to one plate of the pump capacitor CP, the other plate of the pump capacitor receives a master clock control signal CK. It will be appreciated by those skilled in the art that: alternate stages are driven by either the master clock control signal CK or its compliment, i.e. inverse; and the slave control clock signal CK* is derived from the master clock CK such that it operatively controls the level shift circuit 404. The level shift circuit 404 operates so as to effectively level shift the switching voltages of the slave control signal CK* (which switches between VDD* and a reference voltage such as ground for example) such that the gate drive to switch transistor 402 is switched between it's output voltage $V_{OUT}$ and its voltage $V_{OUT}$ minus VDD*.

Now, taking switching losses into account, using the charge pump stage 400 as shown in FIG. 4b, where the current is passed via transistor switch elements 402, consecutive stages are pumped up by a voltage step ΔVDD. Where ΔVDD=VDD*−Vs and where Vs is the voltage drop of the transistor switch 402, i.e. $I.R_{on}$. For minimum size MOS switches on a typical CMOS integrated circuit, $R_{on}$ may be of the order of 2-10 KΩ, and is temperature dependent. Even using such minimum size MOS switches in the charge pump 99 of FIG. 2 where the load current is 60 uA, such minimum size MOS switches would still result in a voltage drop of 120 to 600 mV, or 10-50% of ΔVDD. However, referring back to FIG. 4b, the inventor realised that in the application of biasing a high impedance load, such as a capacitive transducer for example, in a circuit without extra loading on the output 202 of the charge pump 100, the effective load, due to powering the small level shift circuits 404, which is in the order of nanoamps (nA), would not significantly impact the output voltage $V_{CP}$.

Therefore, in an application where the load to be biased has a high input impedance i.e. a load ($C_{MEMS}$) that draws small amounts of current, together with a charge pump architecture with small internal voltage drops across the switching elements 402, i.e. minimum size MOS transistor switches, it transpires that each stage S1-SN of the charge pump 100, and the charge pump 100 as a whole, has a stable and predictable gain. This stability and predictability allows the charge pump 100 to be controlled in an open loop manner. That is to say, a stable and predictable charge pump 100 can have its output voltage $V_{CP}$ regulated by controlling and adjusting its input voltage VDD*.

It is noted that the pass switches 402 in the charge pump 400 have an added advantage in that they never see more than 2.VDD* across their respective terminals, so such switches 402 may advantageously be implemented with transistors rated at 2.5V or 3.3V, as is commonly available as standard transistors in a CMOS process, and which are suitable for use in the amplifier circuitry 101. Also there is no need for any other circuitry to be exposed to the charge pump output voltage $V_{CP}$, thus obviating any need for special high-voltage devices.

Thus, the minimal, i.e high impedance, output load allows the charge pump 100 to be designed with minimum or near-minimum size switches and other elements, thus giving a low switching power consumption and chip area.

FIG. 4b may be adapted so as to include a pin (or nip) diode PD (such as a silicon or polysilicon pin diode), illustrated by dashed lines as disclosed in co-pending patent application P1201 GB00 by the present applicant. The inclusion of such a pin diode PD in each stage 400 provides reverse breakdown protection in respect of the stage transistors in a series of stages S1-SN by providing a leakage path (in the order of nanoamps) from the higher voltage output side ($V_{OUT}$) of each respective stage to its lower voltage input side ($V_{IN}$). The inclusion of such a pin diode PD ensures the orderly power-down of the charge pump 100, while introducing insignificant leakage in normal operation. It should be noted that the application of a pin diode PD for protecting the circuitry, i.e. transistors, in a switching voltage generator stage, such as charge pump for example, and therefore the switching voltage generator itself, is equally applicable to switching stages that comprise high reverse breakdown transistors as well as, or instead of, low reverse breakdown transistors.

It is noted that the means for controlling the input of the voltage generator 100 in FIG. 3 may comprise arrangements other than the amplifier 301 and potential divider circuit 305 shown in FIG. 3

Figure 5:
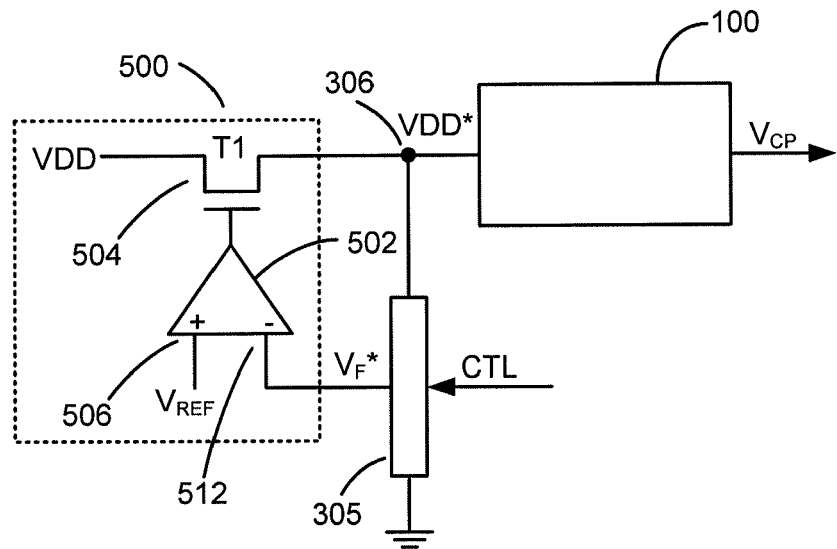
FIG. 5 shows an alternative arrangement to FIG. 3 for adjusting the input voltage of the voltage generator; and, FIG. 6 shows an alternative embodiment for the potential divider shown in FIG. 3.

FIG. 5 illustrates an example of an alternative control circuit to that illustrated in FIG. 3.

For clarity and brevity of explanation only those components directly connected to the alternative control circuit have been illustrated.

Referring to FIG. 5, according to an aspect of the invention a second voltage generator in the form of a voltage regulator circuit, for example a low drop-out regulator 500, is provided for supplying an input voltage VDD* (first voltage) to the input of the first voltage generator, for example a charge pump 100. The charge pump 100 generates an output voltage $V_{CP}$ (second voltage) for biasing the MEMS microphone $C_{MEMS}$ (not illustrated). The low drop-out regulator 500 comprises an amplifier 502, the output of which controls a pass transistor 504, for example an n-type transistor, that acts as a variable resistor. The pass transistor 504 receives a supply voltage VDD (third voltage, for example 1.5 v) and provides an output voltage VDD* which forms the input voltage to the charge pump 100. As described above in respect of FIG. 3, the precise value of the voltage VDD* is adjusted under control of the amplifier 502, based on the value of the voltage VDD* and a feedback signal or calibration value derived from the output of the MEMS microphone $C_{MEMS}$.

The amplifier 502 receives a reference voltage $V_{REF}$ on a first input terminal, for example its non-inverting input 506. The reference voltage $V_{REF}$ is a stable reference voltage, for example a bandgap reference. The second input terminal of the amplifier 502, i.e. its inverting input 512, is coupled to receive a feedback voltage $V_F$ that is set by the potential divider circuit 305.

As discussed above, the potential divider circuit 305 is able to adjust the amount of output voltage VDD* being fed back to the inverting input 512 of the amplifier based on the calibration value received from the automatic test equipment during testing or from memory (not illustrated) i.e. derived from the output of the MEMS microphone $C_{MEMS}$ (not illustrated).

The amplifier 502 compares the voltage received at the inverting input 512 with the reference voltage $V_{REF}$ received at the non-inverting input 506. If the amplifier 502 determines that the output voltage $V_{CP}$ from the charge pump 100 has risen too high relative to the reference voltage $V_{REF}$, the positive supply voltage VDD* being supplied to the charge pump is lowered by controlling the pass transistor 504, i.e. by adjusting the voltage applied to the gate of pass transistor 504, or in other words by adjusting the channel resistance of the pass transistor 504.

In this way, the input voltage VDD* of the charge pump 100 can be controlled based on the voltage signal from the potential divider circuit 305, which in turn is configured according to the calibration value CTL. Upon receipt of an adjusted voltage VDD*, the charge pump 100 in turn provides an adjusted voltage $V_{CP}$ to the MEMS microphone 102.

Figure 6:
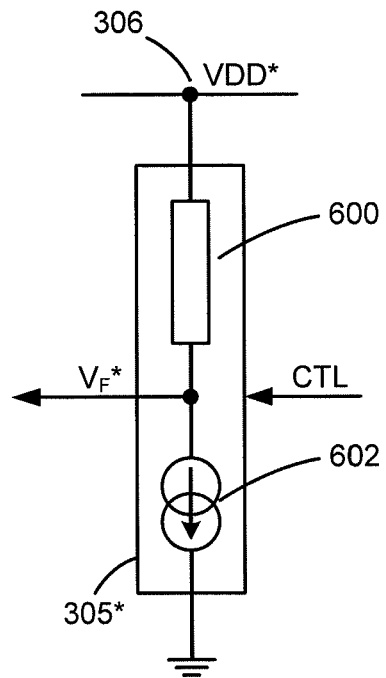

FIG. 6 illustrates an alternative to the potential divider 305 illustrated and described in connection with FIGS. 3 and 5.

Referring to FIG. 6, according to another aspect of the invention an alternative feedback circuit 305* to the potential divider circuit 305 (illustrated in FIGS. 3 and 5) comprises a series connected resistor 600 and current source 602. The high side of the resistor 600 is connected to node 306 to receive the input voltage VDD* to the voltage generator 100 (not illustrated) and its low side is connected to the high side of the current source 602, whose low side is connected to a reference voltage, typically ground.

Either the current source 602 and/or the resistor 600 may be variable in nature such that either one, or both, may be varied in response to the calibration value CTL to output a feedback signal, in the form of a voltage $V_F*$, to the control circuit (300, 500), as illustrated in FIGS. 3 and 5.

The embodiments described above have the advantage of enabling a bias voltage to a high input impedance transducer to be trimmed, tuned or calibrated without having the disadvantages associated with the prior art.

The problem of supplying a stable adjustable bias voltage to a capacitive transducer, while consuming low power and chip area, is solved by driving the input of an open-loop charge pump, that uses switch elements to minimise internal voltage drops despite using (near-)minimum size switches, from a digitally adjustable voltage regulator. This enables a corresponding method for calibrating the sensitivity of the device comprising the transducer, at factory test or later in end use.

It will be appreciated by those skilled in the art that although the invention has been described with reference to a MEMS capacitive transducer, and in particular a MEMS microphone, it is equally applicable to other capacitive transducers or indeed other high input impedance components, circuitry and the like. Furthermore, the type of applications in which such transducers are used are not intended to be limited to audio type applications, the present invention is also applicable to accelerometers, gyroscopes and ultrasound type applications to name just a few.

It is noted that, although the embodiments are based on the input voltage to the voltage generator being controlled from a calibration value provided by test equipment, it will be appreciated that the calibration value may be derived from other sources, for example from a calibration value derived from the output of the capacitive transducer or from a memory element.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference signs in the claims shall not be construed so as to limit their scope.

What is claimed is:

1. An apparatus for biasing a high impedance transducer comprising:
    a first voltage generator configured to receive, in use, a first voltage (VDD*) and generate a second voltage ($V_{CP}$) for biasing the transducer, said second voltage having a stable relationship to said first voltage; and
    a control circuit configured to, in use, control the first voltage (VDD*) based on a calibration value, wherein a different calibration value would lead to a different first voltage level, wherein the control circuit comprises:
        a second voltage generator for generating, in use, the first voltage (VDD*), the second voltage generator receiving, in use, a third voltage ($V_{REF}$); and
        a feedback circuit for controlling the second voltage generator based on the calibration value and the first voltage (VDD*).

2. An apparatus as claimed in claim 1 wherein the control circuit is connected to the input of the first voltage generator and is not connected to the output of the first voltage generator.

3. An apparatus as claimed in claim 1 wherein said control circuit is connected on the input side of the first voltage generator only.

4. An apparatus as claimed in claim 1, wherein the feedback circuit comprises:
    an adjustable potential divider circuit comprising a first resistive value (Ra) and a second resistive value (Rb) connected in series between the first voltage (VDD*) and a first reference voltage (GND);
    wherein the value of at least one of the first resistive value and second resistive value is adjusted using the calibration value; and
    wherein a node connecting the first resistive value and the second resistive value provides a feedback signal ($V_{F*}$) for controlling the second voltage generator.

5. An apparatus as claimed in claim 4, wherein the second voltage generator comprises;
    an amplifier coupled to receive, in use, the third voltage ($V_{REF}$) as a supply voltage, the amplifier comprising:
    a first input terminal coupled to a second reference voltage;
    a second input terminal coupled to the feedback signal ($V_{F*}$); and
    an output terminal providing the first voltage (VDD*).

6. An apparatus as claimed in claim 4, wherein the second voltage generator comprises;
    a transistor (T1) connected in series between the third voltage ($V_{REF}$) and the first voltage (VDD*); and
    an amplifier comprising:
    a first input terminal coupled to a second reference voltage;
    a second input terminal coupled to the feedback signal (VF*); and
    an output terminal for controlling the transistor (T1).

7. An apparatus as claimed in claim 4, wherein the adjustable potential divider circuit comprises an array of resistive values configurable to provide the first resistive value and the second resistive value of the adjustable potential divider circuit.

8. An apparatus as claimed in claim 7, further comprising a plurality of switches, the plurality of switches being controlled by the calibration value to provide the first and second resistive values of the adjustable potential divider circuit.

9. An apparatus as claimed in claim 1 further comprising a transducer, the transducer being biased by the second voltage.

10. An apparatus as claimed in claim 9 wherein the calibration value is set such that the transducer has a calibrated response.

11. An apparatus as claimed in claim 9, wherein the calibration value is derived from test equipment coupled to the output of the transducer.

12. An apparatus as claimed in claim 9, wherein the calibration value is derived directly from an output signal of the transducer.

13. An apparatus as claimed in claim 9, wherein the transducer is a capacitive transducer.

14. An apparatus as claimed in claim 13, wherein the capacitive transducer is a MEMS microphone.

15. An apparatus as claimed in claim 1, wherein the calibration value is received from a memory device of the type comprising a random access memory (RAM), programmable read only memory (PROM), erasable programmable read only memory (EPROM), electrically erasable programmable read only memory (EEPROM), flash memory or field programmable gate array (FPGA), or one or more fuse devices.

16. An apparatus as claimed in claim 1, wherein the first voltage generator is a charge pump.

17. An apparatus as claimed in claim 1 wherein the apparatus comprises one of an ultrasound imager, a sonar transmitter and/or receiver, a mobile phone or other communication device, a personal desktop assistant, an MP3 player or other personal audio device or a laptop computer.

18. A method of biasing a transducer which, in use, receives an input signal and produces an output signal, the method comprising the steps of:
    providing a first voltage generator, the first voltage generator connected to receive a first voltage (VDD*) and generate a second voltage ($V_{CP}$) for biasing the transducer such that the second voltage has a stable relationship to the first voltage; and
    controlling the first voltage (VDD*) based on a calibration value, wherein a different calibration value would lead to a different first voltage level, said controlling also comprising the steps of:
        providing a second voltage generator for generating the first voltage (VDD*), the second voltage generator receiving a third voltage ($V_{REF}$).sub.; and
        controlling the second voltage generator using the calibration value and the first voltage (VDD*).

19. A method as claimed in claim 18, wherein the step of controlling the second voltage generator further comprises the steps of:
    providing an adjustable potential divider circuit comprising a first resistive value (Ra) and a second resistive value (Rb) connected in series between the first voltage (VDD*) and a first reference voltage (GND);
    adjusting the value of at least one of the first resistive value and second resistive value using the calibration value; and
    using a node connecting the first resistive value and the second resistive value as a feedback signal ($V_F*$) for controlling the second voltage generator.

20. A method as claimed in claim 19, wherein the step of providing a second voltage generator for generating the first voltage comprises the steps of:
    providing an amplifier connected to receive the third voltage (VDD) as a supply voltage;
    coupling a second voltage reference to a first input terminal of the amplifier;
    coupling the feedback signal ($V_{F*}$) to a second input terminal of the amplifier; and
    using the output of the amplifier as the first voltage (VDD*).

21. A method as claimed in claim 19, wherein the step of providing a second voltage generator for generating the first voltage comprises the steps of;
    providing a transistor (T1) connected in series between the third voltage (VDD) and the first voltage (VDD*); and
    providing an amplifier comprising a first input terminal coupled to a second reference voltage and a second input terminal coupled to the feedback signal (VF*); and
    controlling the transistor (T1) using an output of the amplifier.

22. A method as claimed in claim 19, wherein the step of providing an adjustable potential divider circuit comprises configuring an array of resistive values to provide the first resistive value and the second resistive value of the adjustable potential divider circuit.

23. A method as claimed in claim 22, further comprising the step of providing a plurality of switches, and controlling the plurality of switches using the calibration value to provide the first and second resistive values of the adjustable potential divider circuit.

24. A method as claimed in claim 18, wherein the calibration value is derived during a test procedure from test equipment connected to the output of the transducer.

25. A method as claimed in claim 18, wherein the calibration value is received from a memory device of the type comprising a random access memory (RAM), programmable read only memory (PROM), erasable programmable read only memory (EPROM), electrically erasable programmable read only memory (EEPROM), flash memory or field programmable gate array (FPGA), or one or more fuse devices.

26. A method as claimed in claim 18, wherein the calibration value is received directly from an output signal of the transducer.

27. A method as claimed in claim 18, wherein the transducer is a capacitive transducer.

28. A method as claimed in claim 27, wherein the capacitive transducer is a MEMS microphone.

29. A method as claimed in claim 18, wherein the first voltage generator is a charge pump.

30. A method of calibrating an apparatus having a transducer which, in use, receives an input signal and produces an output signal, the method comprising the steps of:
    providing a first voltage generator, the first voltage generator connected to receive a first voltage (VDD*) and generate a second voltage ($V_{CP}$) for biasing the capacitive transducer;
    applying at least one test signal to the transducer and monitoring the response; and
    setting a calibration value in a control circuit, the control circuit controlling the first voltage based on the calibration value,
    wherein the control circuit comprises a second voltage generator for generating the first voltage (VDD*), the second voltage generator receiving, in use, a third voltage (V.sub.REF); and a feedback circuit for controlling the second voltage generator based on the calibration value and the first voltage (VDD*).

31. A method as claimed in claim 30 wherein the control circuit is connected on the input side of the first voltage generator only.

32. A method as claimed in claim 30 wherein the feedback circuit comprises:
    an adjustable potential divider circuit comprising a first resistive value (Ra) and a second resistive value (Rb) connected in series between the first voltage (VDD*) and a first reference voltage (GND), a node connecting the first resistive value and the second resistive value providing a feedback signal ($V_{F*}$) for controlling the second voltage generator;
    wherein the step of setting the calibration value comprises adjusting at least one of the first resistive value and second resistive value.

33. A method as claimed in claim 32, wherein the adjustable potential divider circuit comprises an array of resistive values configurable to provide the first resistive value and the second resistive value of the adjustable potential divider circuit and the step of setting the calibration value comprises configuring said resistive values.

34. A method as claimed in claim 33, wherein the adjustable potential divider further comprises a plurality of switches, and the step of setting the calibration value comprises activating at least some of said switches to provide the first and second resistive values of the adjustable potential divider circuit.

35. A method as claimed in claim 30 wherein the step of setting the calibration value comprises storing the calibration value in a memory device of the type comprising a random access memory (RAM), programmable read only memory (PROM), erasable programmable read only memory (EPROM), electrically erasable programmable read only memory (EEPROM), flash memory or field programmable gate array (FPGA), or one or more fuse devices.

* * * * *